United States Patent
Lichtenstein et al.

(10) Patent No.: US 9,339,333 B2
(45) Date of Patent: May 17, 2016

(54) TORSION REDUCTION SYSTEM

(71) Applicant: BIOSENSE WEBSTER (ISRAEL) LTD., Yokneam (IL)

(72) Inventors: Yoav Lichtenstein, Raanana (IL); Ronen Krupnik, Karmiel (IL); Roy Urman, Karkur (IL); Natan Sharon Katz, Kiryat Bialik (IL); Goren Cohn, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 399 days.

(21) Appl. No.: 14/139,974

(22) Filed: Dec. 24, 2013

(65) Prior Publication Data
US 2015/0173829 A1    Jun. 25, 2015

(51) Int. Cl.
*A61B 18/00* (2006.01)
*A61B 18/14* (2006.01)

(52) U.S. Cl.
CPC ... *A61B 18/1492* (2013.01); *A61B 2018/00029* (2013.01); *A61B 2018/00172* (2013.01); *A61B 2018/00178* (2013.01); *A61B 2018/00208* (2013.01); *A61B 2018/00351* (2013.01); *A61B 2018/00577* (2013.01); *A61B 2218/002* (2013.01)

(58) Field of Classification Search
CPC .............. A61B 18/1492; A61B 2018/00029; A61B 2018/00577; A61B 2018/00351; A61B 2018/00208; A61B 2018/00172; A61B 2218/0028
See application file for complete search history.

(56) References Cited

U.S. PATENT DOCUMENTS

| | | | | |
|---|---|---|---|---|
| 4,157,472 | A | * 6/1979 | Beck, Jr. | A61B 6/032 378/194 |
| 5,060,632 | A | * 10/1991 | Hibino | A61B 1/00039 348/65 |
| 5,240,003 | A | * 8/1993 | Lancee | A61B 8/12 310/162 |
| 5,391,199 | A | 2/1995 | Ben-Haim | |
| 5,443,489 | A | 8/1995 | Ben-Haim | |
| 5,558,091 | A | 9/1996 | Acker | |
| 5,582,171 | A | * 12/1996 | Chornenky | A61B 1/00183 600/425 |
| 5,944,022 | A | 8/1999 | Nardella | |
| 5,983,126 | A | 11/1999 | Wittkampf | |
| 6,172,499 | B1 | 1/2001 | Ashe | |
| 6,177,792 | B1 | 1/2001 | Govari | |

(Continued)

OTHER PUBLICATIONS

European Search Report dated Jun. 17, 2015 for corresponding Application No. EP14200169.

*Primary Examiner* — Jaymi Della
*Assistant Examiner* — Eunhwa Kim
(74) *Attorney, Agent, or Firm* — Louis J. Capezzuto (57) ABSTRACT

An apparatus, including an insertion tube having a proximal tube end and a distal tube end that includes an electrode, a first irrigation line including proximal and distal irrigation line ends and configured to supply fluid from the distal irrigation line end through apertures in the tube, and an electrical line including a proximal electrical line end and a distal electric line end coupled to the electrode. The apparatus includes a slip ring unit having a stator, a rotor connected to the proximal electrical line end, and a hollow channel extending through respective centers of the stator and the rotor along a longitudinal axis of the slip ring unit. The apparatus includes a rotary joint in fluid communication with the proximal irrigation line end, an angle sensor configured to detect torsion of the proximal irrigation line end, and a drive mechanism coupled to rotate the rotor responsively to the torsion.

25 Claims, 5 Drawing Sheets

(56) References Cited

U.S. PATENT DOCUMENTS

| | | | | |
|---|---|---|---|---|
| 6,241,744 B1 * | 6/2001 | Imran | ............... | A61B 8/0833 128/898 |
| 6,413,222 B1 * | 7/2002 | Pantages | ............... | A61B 8/12 600/466 |
| 6,456,864 B1 | 9/2002 | Swanson | | |
| 6,464,645 B1 * | 10/2002 | Park | ............... | A61B 1/0052 600/462 |
| 6,690,963 B2 | 2/2004 | Ben-Haim | | |
| 6,788,967 B2 | 9/2004 | Ben-Haim | | |
| 2012/0184955 A1 | 7/2012 | Pivotto et al. | | |
| 2013/0023770 A1 | 1/2013 | Courtney et al. | | |
| 2013/0284479 A1 * | 10/2013 | Chen | ............... | B25F 5/02 173/217 |

* cited by examiner

TORSION REDUCTION SYSTEM

FIELD OF THE INVENTION

The present invention relates generally to invasive probes, and specifically to a system that reduces cable torsion and prevents cable entanglement for an invasive probe having multiple cables connected to a proximal end of the probe.

BACKGROUND OF THE INVENTION

A wide range of medical procedures involve placing objects such as sensors, tubes, catheters, dispensing devices, and implants, within the body. An example of a medical procedure performed with a catheter is ablation of body tissue such as heart tissue. The ablation may be used to cure a variety of cardiac arrhythmia such as atrial fibrillation. Such procedures are known in the art. Other medical procedures using ablation of body tissue, such as treating varicose veins, are also known in the art. The ablation energy for these procedures may be in the form of radio-frequency (RF) energy, which is supplied to the tissue via one or more electrodes of a catheter used for the procedures.

The application of the ablation energy to body tissue, if uncontrolled, may lead to an unwanted increase of temperature of the tissue. It is consequently important to monitor and control the temperature of the tissue during any medical procedure involving ablation. One method for control is to irrigate the tissue being ablated.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention an apparatus, including a flexible insertion tube including a proximal tube end and a distal tube end for insertion into a body cavity, and an electrode mounted at the distal tube end. The apparatus also includes a first irrigation line, including proximal and distal irrigation line ends, contained within the insertion tube, and configured to supply irrigation fluid from the distal irrigation line end through one or more apertures in the distal tube end. The apparatus additionally includes a first electrical line contained within the insertion tube and including a proximal electrical line end and a distal electric line end, which is coupled to the electrode. The apparatus further includes a slip ring unit including a stator connected to a second electrical line for connection to a console, a rotor connected to the proximal electrical line end, and a hollow channel extending through respective centers of the stator and the rotor along a longitudinal axis of the slip ring unit. The apparatus also includes a rotary joint in fluid communication with the proximal irrigation line end, and in fluid communication with the console via a second irrigation line, an angle sensor configured to detect torsion of the proximal irrigation line end and the proximal electrical line end, and a drive mechanism coupled to rotate the rotor responsively to the detected torsion so as to reduce the torsion of the proximal irrigation line end and the proximal electrical line end.

In some embodiments, the body cavity may include a heart, and the probe may include an intracardiac catheter. In additional embodiments, the irrigation fluid may include a saline solution. In further embodiments, the apparatus may include a belt coupling the drive mechanism to the rotor.

In supplemental embodiments, the angle may include a strain gauge. In alternative embodiments, the angle sensor may include a position sensor mounted in the flexible insertion tube, the position sensor configured to detect the torsion by measuring a change of orientation of the flexible insertion tube.

In further embodiments, the apparatus may include a bearing including an internal ring surrounded by an external ring, wherein the internal ring encompasses the proximal irrigation line end, and wherein the angle sensor may include an angle encoder mounted on the external ring, and wherein the angle encoder is configured to detect the torsion by measuring an angle of rotation between the internal and the external rings. In additional embodiments, the angle encoder may include decoding electronics, and the apparatus may include a marked disk mounted on the internal ring.

In supplemental embodiments, the console may include an ablation module and an irrigation module, and wherein the second electrical line connects the ablation module to the stator, and wherein the rotary joint is in fluid communication with the irrigation module via the second irrigation line. In additional embodiments, the proximal irrigation line end is threaded through the hollow channel and connected to the rotary joint.

In some embodiments, the apparatus may include a handle coupled to the proximal tube end, and wherein the detected torsion corresponds to an angle of rotation of the handle, and wherein the drive mechanism is configured to responsively rotate the rotor by the angle of rotation. In supplemental embodiments, the angle sensor may include a position sensor mounted in the handle, the position sensor configured to detect the torsion by measuring a change of orientation of the handle.

There is also provided, in accordance with an embodiment of the present invention a method, including inserting, into a body cavity, a distal end of a flexible insertion tube including a proximal end, the insertion tube containing an electrode mounted at the distal end, a first irrigation line including proximal and distal irrigation line ends, contained within the insertion tube, configured to supply irrigation fluid from the distal irrigation line end through one or more apertures in the distal end, and inserted through a hollow channel extending through a longitudinal axis of a slip ring unit including a stator and a rotor, and a first electrical line including a proximal electrical line end, which is connected to the rotor, and a distal electric line end, which is coupled to the electrode. The method also includes receiving, from an angle sensor, a signal indicating torsion of the proximal irrigation line end and the proximal electrical line end, and rotating, by a drive mechanism, the rotor responsively to the detected torsion so as to reduce the torsion of the proximal irrigation line end and the proximal electrical line end.

There is further provided, in accordance with an embodiment of the present invention a computer software product, operated in conjunction with a probe that is configured for insertion into a body cavity of a patient and includes an electrode mounted at the distal tube end, a first irrigation line including proximal and distal irrigation line ends, contained within the insertion tube, configured to supply irrigation fluid from the distal irrigation line end through one or more apertures in the distal tube end, inserted through a hollow channel extending through respective a longitudinal axis of a slip ring unit including a stator and a rotor, a first electrical line contained within the insertion tube and including a proximal electrical line end, which is connected to the rotor, and a distal electric line end, which is coupled to the electrode. The computer software product includes a non-transitory computer-readable medium, in which program instructions are stored, which instructions, when read by a computer, cause the computer to receive, from an angle sensor, a signal indicating torsion of the proximal irrigation line end and the proximal electrical line end, and to rotate, via a drive mechanism, the rotor responsively to the detected torsion so as to reduce the torsion of the irrigation line and the electrical line.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Various therapeutic procedures such as cardiac ablation use an invasive medical probe such as a catheter that is inserted into a patient's body. During an ablation procedure on a heart, there may be local overheating of the heart surface being ablated, as well as of the heart tissue underlying the surface. The surface overheating may be manifested as charring, and the overheating of the underlying tissue may cause other damage to the tissue, even leading to penetration of the tissue. To control the temperature of the surface and the underlying tissue, the region being ablated may be irrigated with an irrigation fluid, typically saline, in order to prevent charring.

In addition to the risk of charring, overheating of blood in the region being ablated may cause the formation of potentially dangerous blood clots, which can grow and potentially cause a heart attack or a stroke. In some cases the irrigation may reduce blood clot formation by cooling and diluting the blood.

During an ablation procedure using an invasive probe, an operator (e.g., a physician) may rotate the probe's handle in order to position a distal tip of the probe within the body cavity at a desired location. The handle typically has a first end connected to an insertion tube comprising the distal end, and a second end coupled to an irrigation line and an electrical line. As the operator rotates the handle, there may be torsion that can cause entanglement of the electrical and the irrigation lines.

Embodiments of the present invention provide an apparatus for reducing torsion in lines extending from a handle of an invasive probe such as an intracardiac catheter. The lines may comprise an irrigation line and an electrical line that are contained within the handle and the insertion tube, the irrigation line having proximal and distal irrigation line ends, and the electrical line having proximal and distal electrical line ends.

In some embodiments, the apparatus comprises a slip ring unit, a rotary joint and a drive mechanism controlled by a console. As described hereinbelow, a proximal end of the electrical line is connected to a rotor of the slip ring unit, and a proximal end of the irrigation line is threaded through a channel extending through a center of the rotor along a longitudinal axis of the slip ring unit and in fluid communication with the rotary joint. The rotor is also coupled to the drive mechanism, thereby enabling the drive mechanism to rotate the rotor in response to commands received from the console.

In operation, as the operator rotates the handle in order to position the distal tip of the probe within the body cavity, an angle sensor detects torsion of the electrical and the irrigation lines extending from the handle, and the drive mechanism rotates the rotor responsively to the detected torsion, so as to reduce the torsion.

System Description

Figure 1:
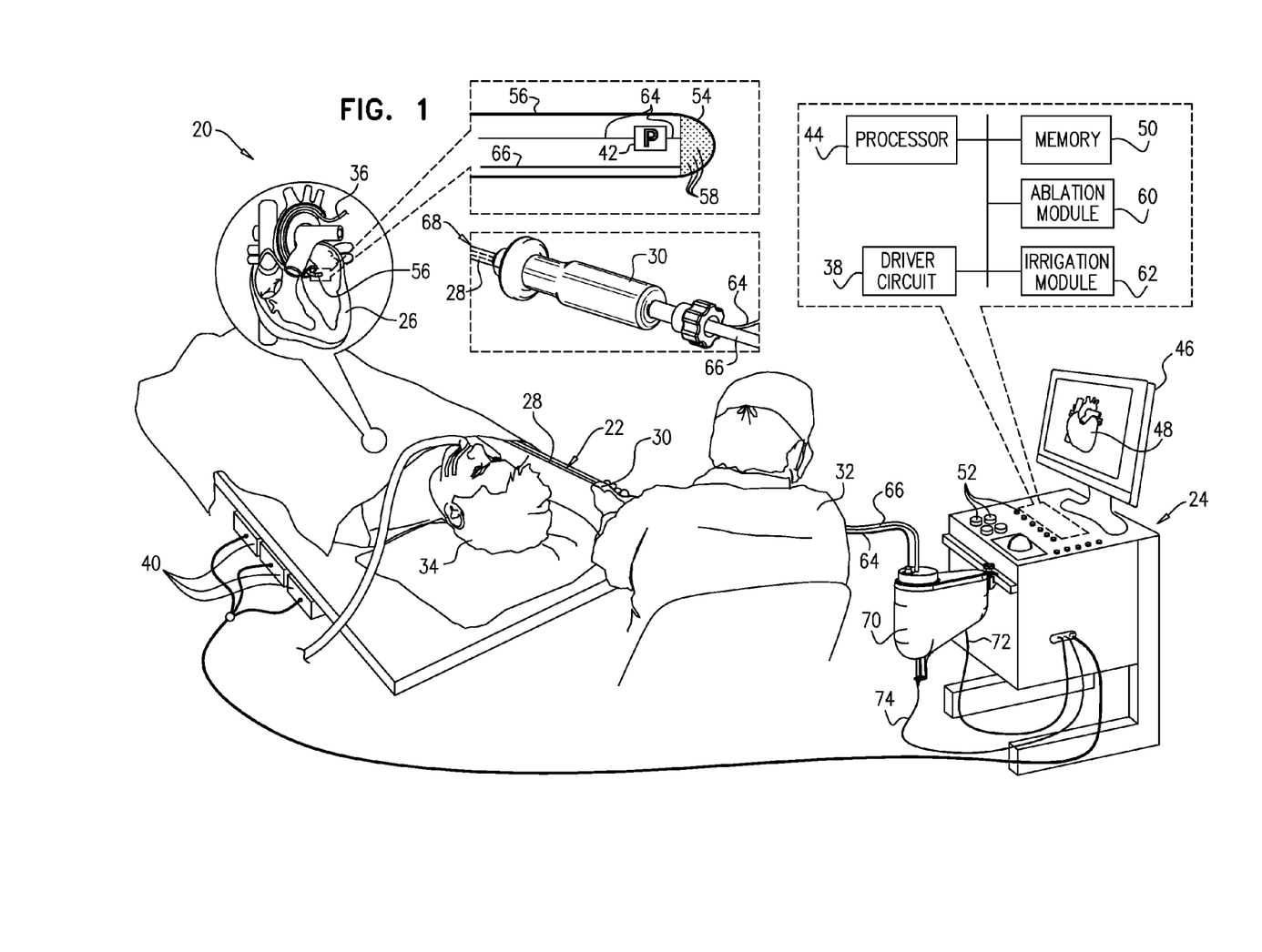
FIG. 1 is a schematic pictorial illustration of a medical system having a torsion management apparatus, in accordance with an embodiment of the present invention.

FIG. 1 is a schematic pictorial illustration of a medical system 20 having a torsion management apparatus 70, in accordance with an embodiment of the present invention. System 20 may be based, for example, on the CARTO™ system, produced by Biosense Webster Inc. (Diamond Bar, Calif.). System 20 comprises a probe 22, such as a catheter, and a control console 24. In the embodiment described hereinbelow, it is assumed that probe 22 is used for diagnostic or therapeutic treatment, such as performing ablation of heart tissue. Alternatively, probe 22 may be used, mutatis mutandis, for other therapeutic and/or diagnostic purposes in the heart or in other body organs.

Probe 22 comprises a flexible insertion tube 28, and a handle 30 coupled to a proximal end 68 of the insertion tube. By manipulating handle 30, an operator 32 can insert probe 22 into a body cavity in a patient 34. For example, operator 32 can insert probe 22 through the vascular system of a patient 34 so that a distal end 36 of probe 22 enters a chamber of heart 26 and engages endocardial tissue at a desired location or locations. Distal end 36 may also be referred to herein as a distal tube end.

System 20 typically uses magnetic position sensing to determine position coordinates of distal end 36 inside heart 26. Console 24 comprises a driver circuit 38 which drives field generators 40 to generate magnetic fields within the body of patient 34. Typically, field generators 40 comprise coils, which are placed below the patient's torso at known positions external to patient 34. These coils generate magnetic fields in a predefined working volume that contains heart 26. A magnetic field sensor 42 (also referred to herein as position sensor 42) within distal end 36 of probe 22 generates electrical signals in response to the magnetic fields from the coils, thereby enabling console 24 to determine the position of distal end 36 within the chamber.

Although in the present example system 20 measures the position of distal end 36 using magnetic-based sensors, other position tracking techniques may be used (e.g., impedance-based sensors). Magnetic position tracking techniques are described, for example, in U.S. Pat. Nos. 5,391,199 and 6,690,963 referenced above, and in in U.S. Pat. Nos. 5,443,489, 6,788,967, 5,558,091, 6,172,499 and 6,177,792, whose disclosures are incorporated herein by reference. Impedance-based position tracking techniques, are described, for example, in U.S. Pat. Nos. 5,983,126, 6,456,864 and 5,944,022, whose disclosures are incorporated herein by reference.

A processor 44 processes these signals in order to determine the position coordinates of distal end 36, typically including both location and orientation coordinates. The method of position sensing described hereinabove is implemented in the above-mentioned CARTO™ system and is described in detail in the patents and patent applications cited above.

Processor 44 typically comprises a general-purpose computer, with suitable front end and interface circuits for receiving signals from probe 22 and controlling the other components of console 24. Processor 44 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 44 may be carried out by dedicated or programmable digital hardware components.

Based on the signals received from probe 22 and other components of system 20, processor 44 drives a display 46 to present operator 32 with an image 48 showing the position of distal end 36 in the patient's body, as well as status information and guidance regarding the procedure that is in progress. Processor 44 stores data representing image 48 in a memory 50. In some embodiments, operator 32 can manipulate image 48 using one or more input devices 52.

In the present embodiment, an electrode 54 is mounted on distal end 36. Electrode 54 typically comprises thin metal layers formed over an insulating sheath 56 of insertion tube 28. In the configuration shown in FIG. 1, electrode 54 has one or more irrigation apertures 58, and irrigation line 66 is configured to supply irrigation fluid from the distal irrigation line end through the one or more apertures in distal end 36.

Console 24 also comprises a radio frequency (RF) ablation module 60 and an irrigation module 62. Processor 44 uses the ablation module to monitor and control ablation parameters such as the level of ablation power applied via electrode 54. The ablation module may also monitor and control the duration of the ablation that is provided.

Console 24 conveys power to position sensor 42 and electrode 54 via an electrical line 64 (also referred to herein as a first electrical line) that is contained within insertion tube 28 and handle 30. Electrical line 64 typically comprises a metallic conductor and has a proximal electrical line end and a distal electric line end that is coupled to electrode 54. While (for illustrative purposes) FIG. 1 shows a single electrical line 64 coupling the electrode and the sensors, there can be multiple connecting cables contained within the insertion tube and the handle.

Typically, during ablation, heat is generated in the electrode (or electrodes) providing the ablation, as well as in the surrounding region. In order to dissipate the heat and to improve the efficiency of the ablation process, system 20 supplies irrigation fluid to distal end 36 via an irrigation line 66 (also referred to herein as a first irrigation line) that has proximal and distal irrigation line ends. System 20 uses irrigation module 62 to monitor and control irrigation parameters, such as the pressure and the temperature of the irrigation fluid. The irrigation fluid is typically normal saline solution, and the rate of flow of the fluid, controlled by irrigation module 62, is typically in the range of approximately 10-20 cc/minute, but may be higher or lower than this range.

Handle 30 is coupled to proximal end 68 of insertion tube 28. Proximal end 68 may also be referred to herein as a proximal tube end. In embodiments of the present invention, insertion tube 28 and handle 30 contain electrical line 64 and irrigation line 66, and the proximal ends of lines 64 and 66 extend from handle 30 and are connected to torsion management apparatus 70, as described hereinbelow. An electrical line 72 (also referred to herein as a second electrical line) couples, via torsion management apparatus 70, electrical line 64 to ablation module 60, and an irrigation line 74 (also referred to herein as a second irrigation line) couples irrigation line 66 to irrigation module 62 via the torsion management apparatus.

In some embodiments, handle 30 may implement compression and/or sampling for magnetic analog signal (MAG) data, electrocardiography (ECG) data, and other data. In additional embodiments, probe 22 may communicate with console 24 via wireless digital communication or via optical communication.

Figure 2:
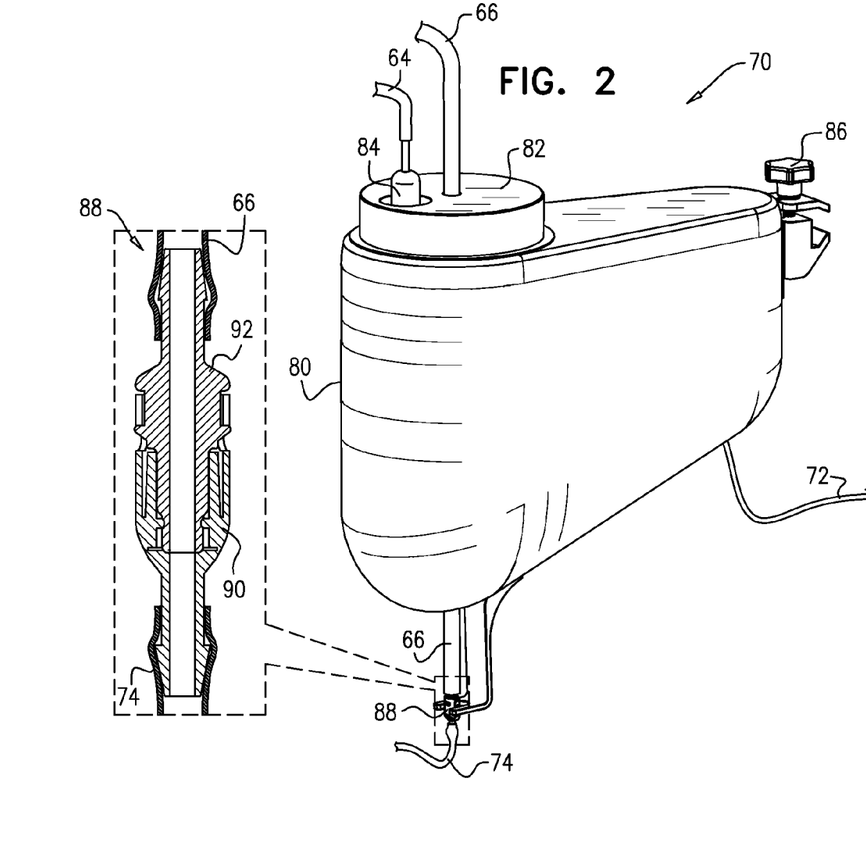
FIG. 2 is a schematic pictorial illustration of an exterior of the torsion management apparatus, in accordance with an embodiment of the present invention.
Figure 6:
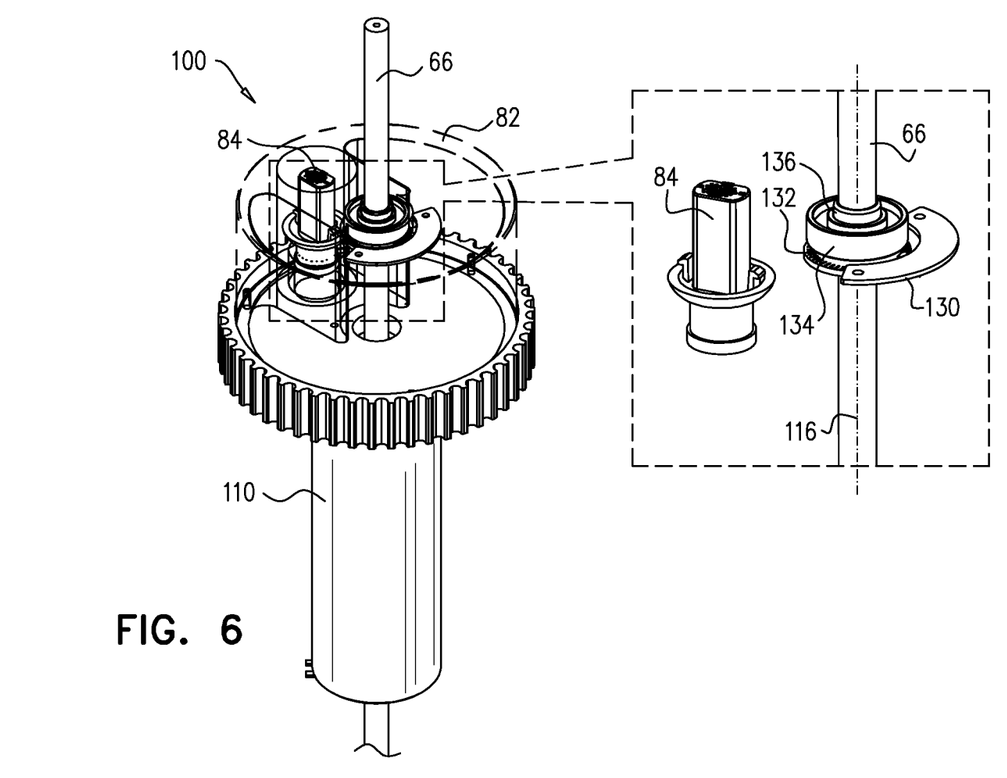
FIG. 6 is a schematic pictorial illustration of an example of an angle sensor used in the torsion management apparatus, in accordance with an embodiment of the current invention.

FIG. 2 is a schematic pictorial illustration of the exterior of torsion management apparatus 70, in accordance with an embodiment of the present invention. The exterior comprises a casing 80, a removable cover 82 having an electrical connector (the cover and the connector are also illustrated in FIG. 6) that connects apparatus 70 to electrical line 64, a mounting clamp 86, and a rotary joint 88 that is affixed to casing 80 and is in fluid communication with the proximal end of irrigation line 66, and is in fluid communication with irrigation module 62 in console 24 via irrigation line 74.

Operator 32 can use mounting clamp 86 to affix apparatus 70 to a fixture in proximity to the operator and the patient, such as console 24 (as shown in FIG. 1) or the patient's bed. In some embodiments, rotary joint 88 comprises a ball and socket joint having a socket 90 holding a ball 92. In the configuration shown in FIG. 2, the proximal end of irrigation line 66 is connected to ball 92 and a distal end of irrigation line 74 is connected to socket 90.

Figure 3:
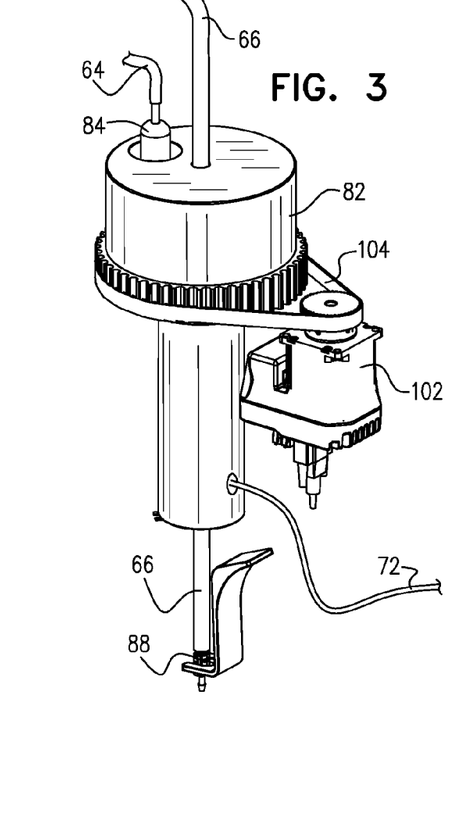
FIG. 3 is a schematic pictorial illustration showing interior elements of the torsion management apparatus, in accordance with an embodiment of the present invention.
Figure 4:
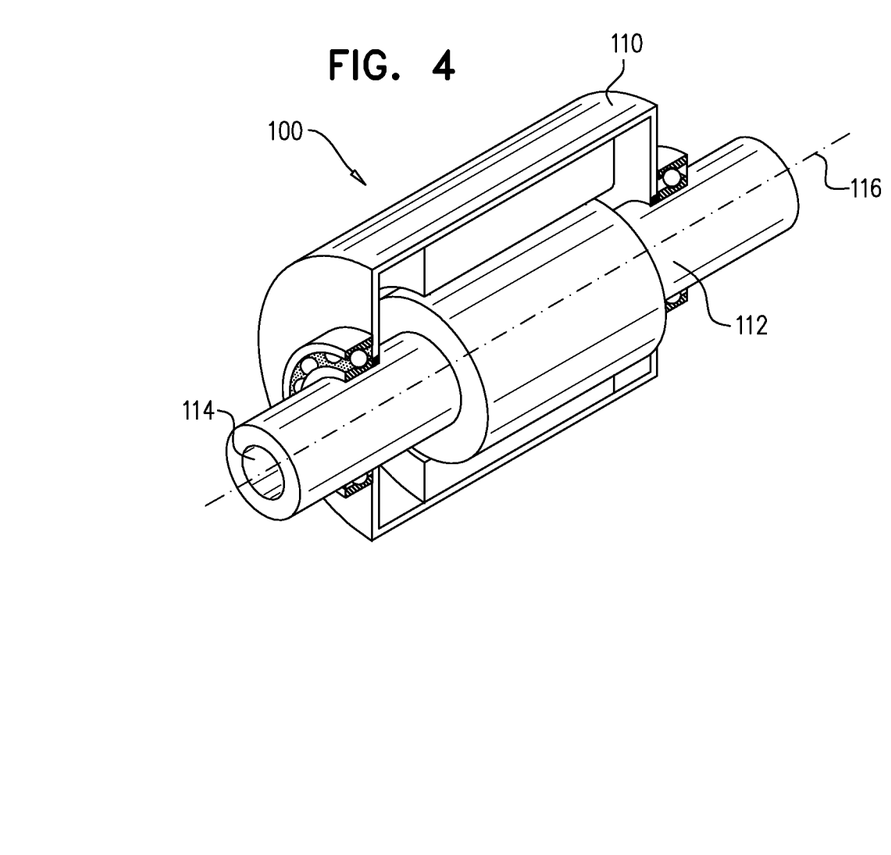
FIG. 4 is a schematic cross-sectional longitudinal view showing details of a slip ring unit used in the torsion management apparatus, in accordance with an embodiment of the present invention.
Figure 5:
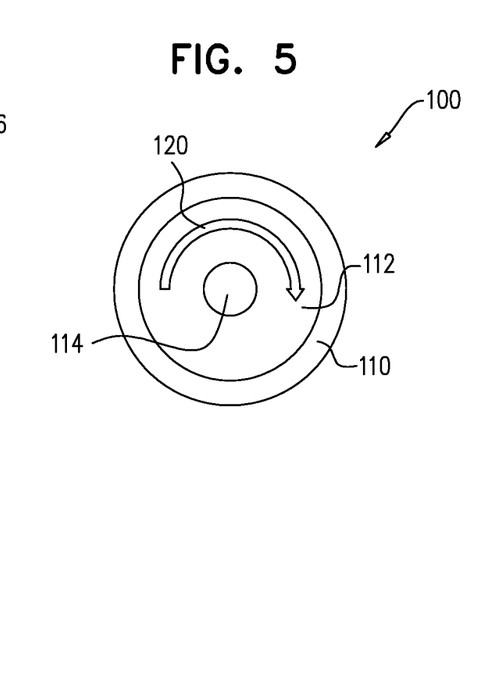
FIG. 5 is a schematic cross-sectional latitudinal view of the slip ring unit, in accordance with an embodiment of the present invention.

FIG. 3 is a schematic pictorial illustration showing interior elements of apparatus 70 comprising a slip ring unit 100, FIG. 4 is a schematic cross-sectional longitudinal view showing details of the slip ring unit, and FIG. 5 is a schematic cross-sectional latitudinal view of the slip ring unit, in accordance with an embodiment of the present invention. The internal elements comprise slip ring unit 100, a drive mechanism (e.g., a motor) 102 and a belt 104.

A slip ring unit is an electromechanical device that allows the transmission of power and electrical signals from a stationary to a rotating structure, or vice versa. In the configuration shown in FIG. 4, slip ring unit 100 comprises a stator 110 encompassing a rotor 112, and belt 104 is connected to drive mechanism 102 and the rotor, thereby enabling the drive mechanism to rotate the rotor, as shown by an arrow 120 in FIG. 5.

Typically, a conductive brush (not shown) is fixedly attached to rotor 112, and the brush makes contact with a conductive ring (not shown) mounted on the interior surface of stator 110. In operation, as rotor 112 rotates, the brush maintains contact with the ring, thereby maintaining an electrical connection between the rotor and the stator. Each ring-brush pair is typically referred to as a slip ring, and slip ring unit 100 may comprise multiple slip rings (i.e., ring-brush pairs) thereby enabling the slip ring unit to convey multiple signals between the stator and the rotor.

Rotor 112 is connected to a proximal end of electrical line 64, and drive mechanism 102 is controlled by processor 44. In other words, the rotation of rotor 112 is controlled by processor 44. In addition to rotating rotor 112, apparatus 70 is configured to enable drive mechanism 102 to rotate the rotor and cover 82 at an identical angular phase as the rotor's rotation.

As shown in FIG. 3, a distal end of electrical line 72 is connected to stator 110, and a proximal end of the second electrical line is connected is connected to ablation module 60. In some embodiments, electrical line 72 may be coupled to one or more other modules of console 24 (i.e., in addition to ablation module 60).

Slip ring unit 100 comprises a hollow channel 114 extending through respective centers of stator 110 and rotor 112 along a longitudinal axis 116 of the slip ring unit. Hollow channel 114 is configured to allow the proximal end of irrigation line 66 to be threaded through the hollow channel and affixed to ball 92 of rotary joint 88.

In embodiments of the present invention, processor 44 receives signals from an angle sensor that is configured to detect torsion of the proximal ends of electrical line 64 and irrigation line 66. The torsion is typically due to operator 32 rotating handle 30 along the handle's longitudinal axis, thereby rotating insertion tube 28 within patient 34.

FIG. 6 is a schematic pictorial illustration of an example of an angle sensor, in accordance with an embodiment of the current invention. In the example shown in FIG. 6, the angle sensor comprises an angle encoder 130 mounted on a bearing 132. Angle encoder 130 typically comprises a printed circuit board having decoding electronics configured to detect an angular offset around longitudinal axis 116.

In the configuration shown in FIG. 6, bearing 132 comprises an internal ring 134 surrounded by an external ring 136 that is fixedly attached to casing 80. Internal ring 134 encompasses and holds the proximal end of irrigation line 66, thereby preventing any axial motion of the proximal end of the first irrigation line relative to the internal ring. In some embodiments, a marked disk is mounted on the internal ring, and the decoding electronics are mounted on the external ring. The marked disk typically comprises a disk having physical markings or slots embedded in the disk.

Therefore, operator 32 rotating handle 30 causes a corresponding rotation of internal ring 134 (the internal ring is holding a portion of the proximal end of irrigation line 66), and angle encoder 130 can measure an angle of rotation between the internal ring and the external ring, and convey an angle encoder signal to processor 44 indicating the angle of rotation, thereby indicating torsion of the proximal irrigation line end and the proximal electrical line end.

While the example in FIG. 6 shows angle encoder 130 configured as an angle sensor, other types of angle sensors are considered to be within the spirit and scope of the present invention. For example, the angle sensor may comprise a strain gauge (not shown) configured to measure any strain on electrical line 64 and/or irrigation line 66, typically as a result of operator 32 rotating handle 30.

As described supra, position sensor 42 can convey signals to processor 44 indicating location and orientation coordinates of distal end 36. As operator 32 rotates handle 30, there is a corresponding rotation of distal end 36, the proximal irrigation line end and the proximal electrical line end. Therefore, by measuring a change of orientation (i.e., a rotation) of distal end 36, and conveying, to processor 44, a position signal indicating the change of orientation, position sensor 42 may be configured to operate as an angle sensor in system 20.

Additionally, while the configuration shown in FIG. 1 shows position sensor 42 mounted in the distal end of insertion tube 28, the position sensor configured to function as an angle sensor may be positioned in other portions of probe 22. For example, position sensor 42 may be mounted in any part of insertion tube 28 and configured to detect the torsion by measuring a change of orientation of the insertion tube. Alternatively, position sensor may be mounted in handle 30 and configured to detect the torsion by measuring a change of orientation of the handle.

Figure 7:
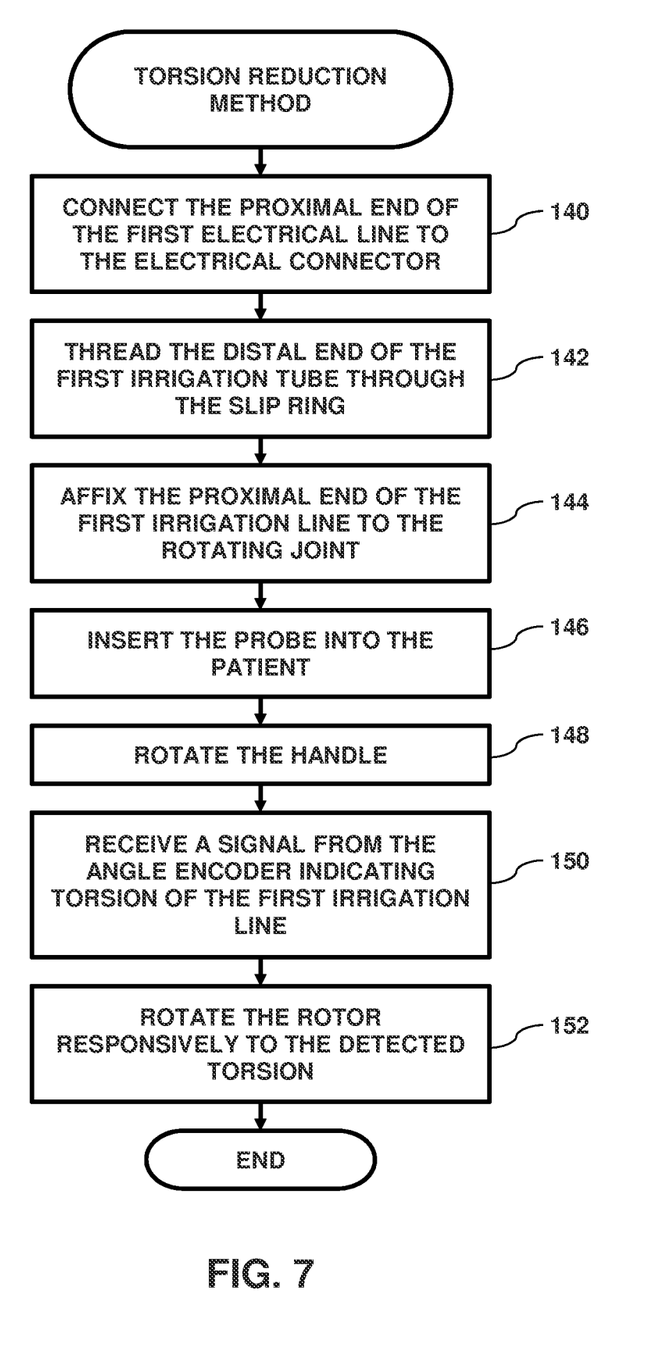
FIG. 7 is a flow diagram that schematically illustrates a method of reducing torsion in electrical and irrigation lines of the medical system, in accordance with an embodiment of the present invention.

FIG. 7 is a flow diagram that schematically illustrates a method of reducing torsion of electrical line 64 and irrigation line 66, in accordance with an embodiment of the present invention. In a connection step 140, operator 32 connects the proximal end of electrical line 64 to connector 84, threads the proximal end of irrigation line 66 through hollow channel 114 of slip ring unit 100 in a threading step 142, and affixes the proximal end of the first irrigation line to ball 92 of rotary joint 88 in an affix step 144.

In an insertion step 146, operator 32 inserts insertion tube 28 of probe 22 into patient 34, and rotates insertion tube by rotating handle 30 in a first rotation step 148. As operator 32 rotates handle 30, the proximal ends of electrical line 64 and irrigation line 66 that extend from handle 30 to apparatus 70 start "twisting" due to the handle's rotation.

In a receive step 150, processor 44 receives a signal from angle encoder 130 indicating torsion of the proximal irrigation line end. In some embodiments, the torsion indicated in the signal corresponds to an angle of rotation of handle 30.

Finally, in a second rotation step 152, processor 44 conveys a signal indicating the angle of rotation of handle 30 to drive mechanism 102, drive mechanism 102 rotates rotor 112 by the angle of rotation, and the method ends. By rotating rotor 112 by the angle of rotation, embodiments of the invention reduce the torsion in proximal ends of irrigation line 66 and electrical line 64, thereby preventing a potential entanglement of the proximal irrigation line end and the proximal electrical line end.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
   a flexible insertion tube comprising a proximal tube end and a distal tube end for insertion into a body cavity;
   an electrode mounted at the distal tube end;
   a first irrigation line, comprising proximal and distal irrigation line ends, contained within the flexible insertion tube, and configured to supply irrigation fluid from the distal irrigation line end through one or more apertures in the distal tube end;
   a first electrical line contained within the flexible insertion tube and comprising a proximal electrical line end and a distal electric line end, which is coupled to the electrode;
   a slip ring unit comprising:
      a stator connected to a second electrical line for connection to a console;
      a rotor connected to the proximal electrical line end; and
      a hollow channel extending through respective centers of the stator and the rotor along a longitudinal axis of the slip ring unit;

a rotary joint in fluid communication with the proximal irrigation line end, and in fluid communication with the console via a second irrigation line;

an angle sensor configured to detect torsion of the proximal irrigation line end and the proximal electrical line end; and a drive mechanism coupled to the rotor and configured to rotate the rotor responsively based upon the torsion detected by the angle sensor so as to reduce the torsion of the proximal irrigation line end and the proximal electrical line end.

2. The apparatus according to claim 1, wherein the body cavity comprises a heart, and the flexible insertion tube comprises an intracardiac catheter.

3. The apparatus according to claim 1, further comprises a belt configured to couple the drive mechanism to the rotor.

4. The apparatus according to claim 1, wherein the angle sensor comprises a strain gauge.

5. The apparatus according to claim 1, wherein the angle sensor comprises a position sensor mounted in the flexible insertion tube, the position sensor configured to detect the torsion by measuring a change of orientation of the flexible insertion tube.

6. The apparatus according to claim 1, further comprises a bearing comprising an internal ring surrounded by an external ring, wherein the internal ring encompasses the proximal irrigation line end, and wherein the angle sensor comprises an angle encoder mounted on the external ring, and wherein the angle encoder is configured to detect the torsion by measuring an angle of rotation between the internal and the external rings.

7. The apparatus according to claim 6, further comprises a marked disk mounted on the internal ring and wherein the angle encoder comprises decoding electronics.

8. The apparatus according to claim 1, wherein the console comprises an ablation module and an irrigation module, and wherein the second electrical line connects the ablation module to the stator, and wherein the rotary joint is in fluid communication with the irrigation module via the second irrigation line.

9. The apparatus according to claim 1, wherein the proximal irrigation line end is threaded through the hollow channel and connected to the rotary joint.

10. The apparatus according to claim 1, further comprises a handle coupled to the proximal tube end, and wherein the detected torsion corresponds to an angle of rotation of the handle, and wherein the drive mechanism is configured to responsively rotate the rotor by the angle of rotation.

11. The apparatus according to claim 10, wherein the angle sensor comprises a position sensor mounted in the handle, the position sensor configured to detect the torsion by measuring a change of orientation of the handle.

12. A method, comprising:
inserting, into a body cavity, a distal end of a flexible insertion tube, wherein the flexible insertion tube comprises:
an electrode mounted at the distal end of the flexible insertion tube,
a first irrigation line comprising proximal and distal irrigation line ends, contained within the flexible insertion tube, configured to supply irrigation fluid from the distal irrigation line end through one or more apertures in the distal end of the flexible insertion tube and inserted through a hollow channel extending through a longitudinal axis of a slip ring unit comprising a stator and a rotor, and a first electrical line comprising a proximal electrical line end, which is connected to the rotor, and a distal electric line end, which is coupled to the electrode;

receiving a signal from an angle sensor indicating torsion of the proximal irrigation line end and the proximal electrical line end; and rotating, by a drive mechanism, the rotor responsively based upon the signal indicating the torsion so as to reduce the torsion of the proximal irrigation line end and the proximal electrical line end.

13. The method according to claim 12, wherein the body cavity comprises a heart, and the probe comprises an intracardiac catheter.

14. The method according to claim 12, wherein the irrigation fluid comprises a saline solution.

15. The method according to claim 12, wherein the drive mechanism rotates the rotor via a belt.

16. The method according to claim 12, wherein the angle sensor comprises a strain gauge.

17. The method according to claim 12, wherein the angle sensor comprises a position sensor mounted in the flexible insertion tube, and wherein receiving the signal comprises receiving, from the position sensor, a position sensor signal indicating a change of orientation of the flexible insertion tube.

18. The method according to claim 12, wherein the angle sensor comprises an angle encoder mounted on an external ring of a bearing, the external ring surrounding an internal ring of the bearing, the internal ring encompassing the proximal irrigation line end, and wherein receiving the signal comprises receiving, from the angle encoder, an angle encoder signal indicating an angle of rotation between the internal and the external rings.

19. The method according to claim 18, wherein the angle encoder comprises decoding electronics, and wherein the bearing comprises a marked disk mounted on the internal ring.

20. The method according to claim 12, wherein the proximal irrigation line end is threaded through the hollow channel and connected to a rotary joint.

21. The method according to claim 12, and comprising a handle coupled to a proximal end of the flexible insertion tube and wherein the signal indicating the torsion corresponds to an angle of rotation of the handle, and wherein the drive mechanism is configured to responsively rotate the rotor by the angle of rotation of the handle.

22. The method according to claim 21, wherein the angle sensor comprises a position sensor mounted in the handle, and wherein receiving the signal comprising receiving, from the position sensor, a position sensor signal indicating a change of orientation of the handle.

23. The method according to claim 12, wherein the stator is connected to a second electrical line for connection to a console, and wherein the hollow channel extends through respective centers of the stator and the rotor along a longitudinal axis of the slip ring unit, and comprising conveying the irrigation fluid from the proximal irrigation line end to a rotary joint in fluid communication with the console via a second irrigation line.

24. The method according to claim 23, wherein the console comprises an ablation module and an irrigation module, and wherein the second electrical line connects the ablation module to the stator, and wherein the rotary joint is in fluid communication with the irrigation module via the second irrigation line.

25. A computer software product, operated in conjunction with a flexible insertion tube comprising a proximal tube end and a distal tube end and is configured for insertion into a body cavity of a patient and wherein the flexible insertion tube includes:
- an electrode mounted at the distal tube end,
- a first irrigation line comprising proximal and distal irrigation line ends, contained within the insertion tube, configured to supply irrigation fluid from the distal irrigation line end through one or more apertures in the distal tube end, inserted through a hollow channel extending through and aligning with a longitudinal axis of a slip ring unit comprising a stator and a rotor,
- a first electrical line contained within the insertion tube and comprising a proximal electrical line end, which is connected to the rotor, and a distal electric line end, which is coupled to the electrode,
- the computer software product comprising a non-transitory computer-readable medium, in which program instructions are stored, which when read by a computer, cause the computer:
    - to receive, from an angle sensor, a signal indicating torsion of the proximal irrigation line end and the proximal electrical line end, and
    - to rotate, via a drive mechanism, the rotor responsively to the signal indicating the torsion so as to reduce the torsion of the first irrigation line and the first electrical line.

\* \* \* \* \*